United States Patent [19]

Burkhart, Jr. et al.

[11] Patent Number: 5,529,807

[45] Date of Patent: Jun. 25, 1996

[54] COMPOSITION AND METHOD FOR TREATING HEAT EXCHANGE SURFACES

[75] Inventors: Lynn Burkhart, Jr., 4653 Casa Grande Ct., Orlando, Fla. 32809; Paul R. Pomp, Scottsdale, Ariz.

[73] Assignee: Lynn Burkhart, Jr., Clearwater, Fla.

[21] Appl. No.: 152,178

[22] Filed: Nov. 12, 1993

(Under 37 CFR 1.47)

[51] Int. Cl.⁶ .............................. B05D 3/02; A01N 25/08
[52] U.S. Cl. ....................... 427/372.2; 427/421; 424/409; 165/133
[58] Field of Search .................................. 424/405, 407; 427/388.4, 372.2, 421

[56] References Cited

U.S. PATENT DOCUMENTS

| | | | |
|---|---|---|---|
| 3,085,908 | 4/1963 | Morehouse et al. | 427/388.4 |
| 3,591,328 | 7/1971 | Szappanyos et al. | 21/58 |
| 4,741,393 | 5/1988 | Collier | 165/133 |
| 4,780,333 | 10/1988 | Smith et al. | 427/236 |
| 4,957,948 | 9/1990 | Terry et al. | 523/122 |
| 5,061,485 | 10/1991 | Oakes et al. | 424/81 |
| 5,238,682 | 8/1993 | Akasaka et al. | 424/409 |
| 5,262,150 | 11/1993 | Laugier et al. | 424/409 |

*Primary Examiner*—Peter F. Kulkosky
*Attorney, Agent, or Firm*—Allen, Dyer, Doppelt, Franjola & Milbrath

[57] ABSTRACT

A composition containing an antimicrobial and a silicone-based emulsion is disclosed for treating heat exchange surfaces. The liquid formulation retards microbial growth and prevents debris from adhering to the surfaces, thus minimizing fouling. The composition does not form a film on the treated surfaces, but rather clings via ionic interaction; thus the heat transfer characteristics of the system are not substantially altered. In addition, the composition does not contain any volatile organic compounds, which can be harmful to a building's occupants. An application method is further disclosed that entails spraying the composition into the cooling coils to be treated, drawing the composition across the heat exchange surfaces in an air stream, and drying the surfaces. This method results in the formation of a low-friction antimicrobial deposit that will resist fouling and microbial growth.

7 Claims, 5 Drawing Sheets

COMPOSITION AND METHOD FOR TREATING HEAT EXCHANGE SURFACES

BACKGROUND OF INVENTION

1. Field of Invention

The invention relates generally to air handling systems, and, more particularly, to compositions and methods of treating air handling systems to prevent microbial buildup and fouling of cooling coils.

2. Description of Related Art

Indoor air quality is a subject of great concern at present, since problems therewith are known to cause illnesses in the building's occupants, a condition known as "sick building syndrome." The primary source for this condition typically lies in the heating, ventilating, and air conditioning (HVAC) system, which can introduce particulates and microorganisms into the air the occupants are forced to breathe. This problem is compounded by most modern buildings being sealed from outdoor air except through the HVAC system, since windows are typically not openable.

The air that is pulled into a building's air handling system is filled with particulates such as dirt, mold spores, microorganisms, and pollen; most of these measure below 10 micrometers, which can easily pass through the filters commonly used at the HVAC system inlet.

Incoming air next usually proceeds through a cooling coils, which normally has 14–18 fins per inch, with approximately 1/16" between adjacent fins. During operation, these fins have a film of condensed water on their surfaces. When the particulate-laden air impinges on the coil, the condensate collects the debris and washes a portion of it into a drip pan, with the remainder adhering to the coils, on which mold and other microorganism growth may occur.

As a matter of practice, coils are cleaned with an acid or caustic cleaner. Since aluminum or copper, the materials of construction of most coil fins, are amphoteric metals, they will corrode in the presence of such cleaners. Such corrosion causes microscopic pitting on coil surfaces, which later harbor and are repositories for contamination such as dirt, microbial growth, and other debris.

The high velocity of air passing across the cooling coil then causes the debris to form an aerosol that is carried by the air stream, is breathed by the building's occupants, and contaminates duct work.

Several attempts have been made in the past to overcome the problems associated with airborne particulates circulated by HVAC systems. Mostly these attempts relate to sprays, coatings, or some related liquid being sprayed or otherwise applied to interiors of the HVAC system. There materials generally contain volatile organic compounds (VOCs). In recent years, increasingly strict legislation has been enacted restricting VOC use.

Smith et al. (U.S. Pat. No. 4,780,333) teaches the use of a deodorizer and antimicrobial coating to treat an air conditioning system. Szappannyos and Eckerman (U.S. Pat. No. 3,591,328) discloses a method of treating air conditioning coils with a fungicide by spraying into an air stream while the air conditioner is operating. Demuth (U.S. Pat. No. 3,493,323) teaches a process of spraying a sterilizing agent through a nozzle into HVAC ducts and then spraying them with a hot fluid, which must subsequently be drained.

Wachman et al. (U.S. Pat. No. 5,124,359) discloses a biocidal aqueous composition for spraying on nonabsorbent surfaces for use on dental and medical equipment. Similarly, Oakes et al. (U.S. Pat. No. 5,061,485) teaches another germicidal composition for disinfecting surfaces. McCoy et al. (U.S. Pat. No. 5,122,301) discloses various antimicrobial compositions but does not include a method of application.

Hayashi et al. (U.S. Pat. No. 4,783,006) describes a mist-dispensing device for forming a thin film on a substrate.

Terry et al. (U.S. Pat. No. 4,957,948) teaches a biocidal protective coating and method for coating heat exchange coils. The coating comprises a polymeric composition comprising an organic water-resistant polymer that bonds to the surface of the coils and a substituted phosphoric acid compound. The method for coating is broadly disclosed as "dipping, brushing or spraying the coils."

There are many problems with currently used compositions and their methods of applications: (1) They usually contain a harmful biocide that can be toxic during application; (2) they may contain volatile organic compounds, which are hazardous to the person applying them, negatively impact indoor air quality for the building occupants, and are restricted by law; (3) their surface coverage may reduce the heat transfer characteristics of the coils, which may cause compressor burnout and increase operating costs; (4) most are not designed to reduce coil fouling; and (5) the depth to which the composition penetrates during application is insufficient for coils over 2 inches deep.

It is thus an object of this invention to provide a composition and method for treating cooling coil surfaces that is capable of minimizing microorganism growth.

It is another object to provide a composition and method that will retain its biocidal characteristics for up to a year.

It is a further object to provide a composition that contains neither a highly toxic biocide nor any volatile organic compounds and is thus not harmful to the building occupants or the applier.

Another object is to provide a composition and method that does not form a film on metal surfaces and thus does not substantially alter the heat transfer characteristics of heat exchange surfaces. Instead, the composition clings to the coils via ionic interaction.

Yet a further object is to provide a composition whose application will prevent debris from adhering to heat exchange surfaces and thus minimize fouling.

It is another object to provide a method of applying a protective composition that ensures the coverage of even the deepest coils within the heat exchanger.

SUMMARY OF THE INVENTION

The present invention comprises an antimicrobial composition and method for coating heat exchangers.

The composition comprises a base and an antimicrobial agent. The viscous base in a preferred embodiment comprises a high-solids oil-in-water emulsion, silicone-based formulation. The silicone composition, which is hydrophobic in nature, has been found to prevent debris from sticking to the heat exchange surfaces and thus provides an antifouling property. The antimicrobial agent is chosen to have a low toxicity so that the application process is safer than prior art products and further so that the building occupants are not exposed to harmful substances. However, any microbial can be used.

The application method comprises providing the above-described composition and applying it to a heat exchange surface to form a low-friction, antimicrobial deposit thereon.

The application step comprises drawing the composition across the heat exchange surface in an air stream. A further step, wherein the composition is in liquid form, comprises drying the composition on the heat exchange surface.

The features that characterize the invention, both as to organization and method of operation, together with further objects and advantages thereof, will be better understood from the following description used in conjunction with the accompanying drawings. It is to be expressly understood that the drawings are for the purpose of illustration and description and are not intended as a definition of the limits of the invention. These and other objects attained, and advantages offered, by the present invention will become more fully apparent as the description that now follows is read in conjunction with the accompanying drawings.

DETAILED DESCRIPTION OF THE PREFERRED EMBODIMENT

Figure 1:
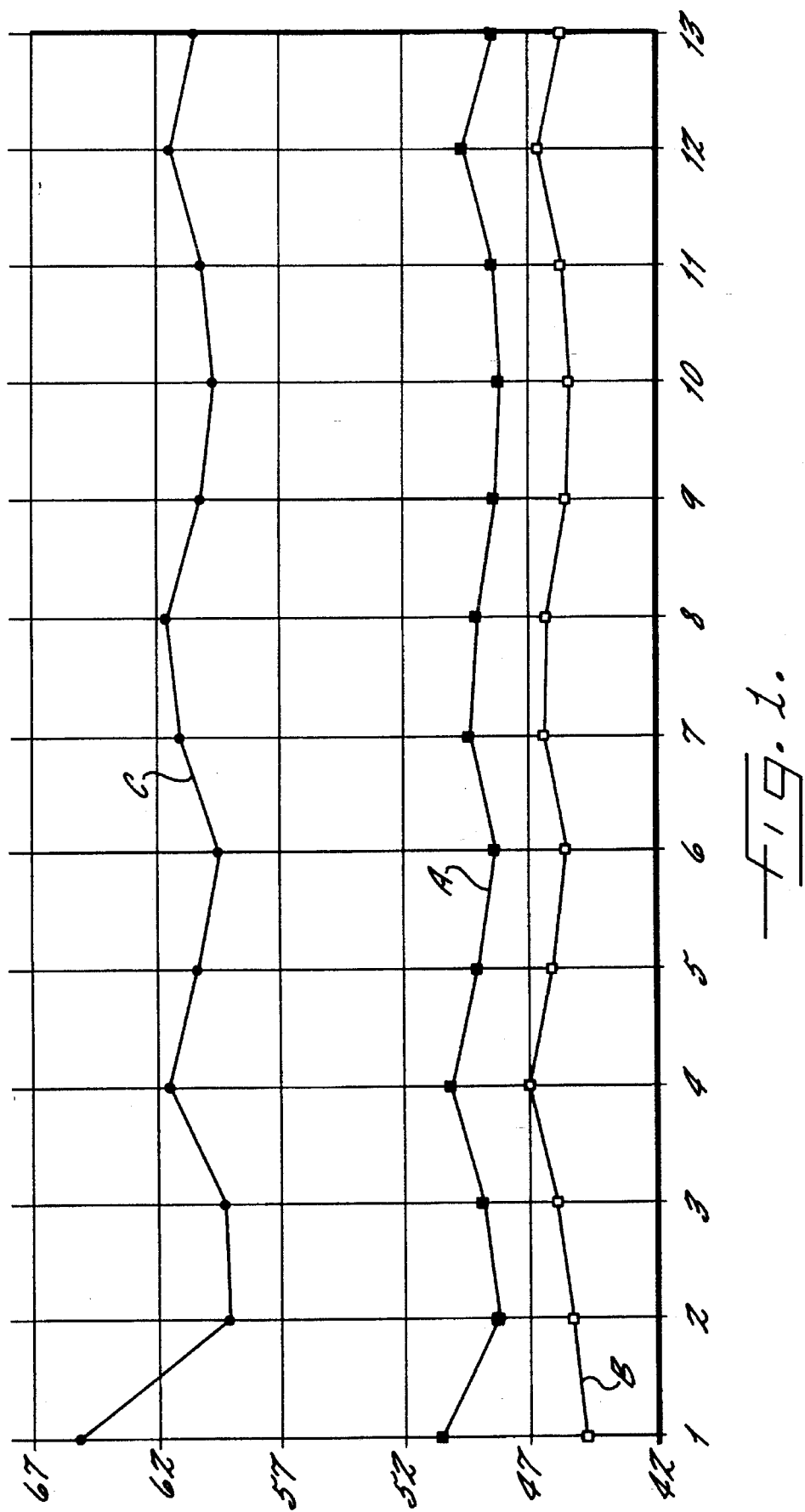
FIG. 1 depicts base temperatures for a unit without the composition of the present invention having been applied.
Figure 2:
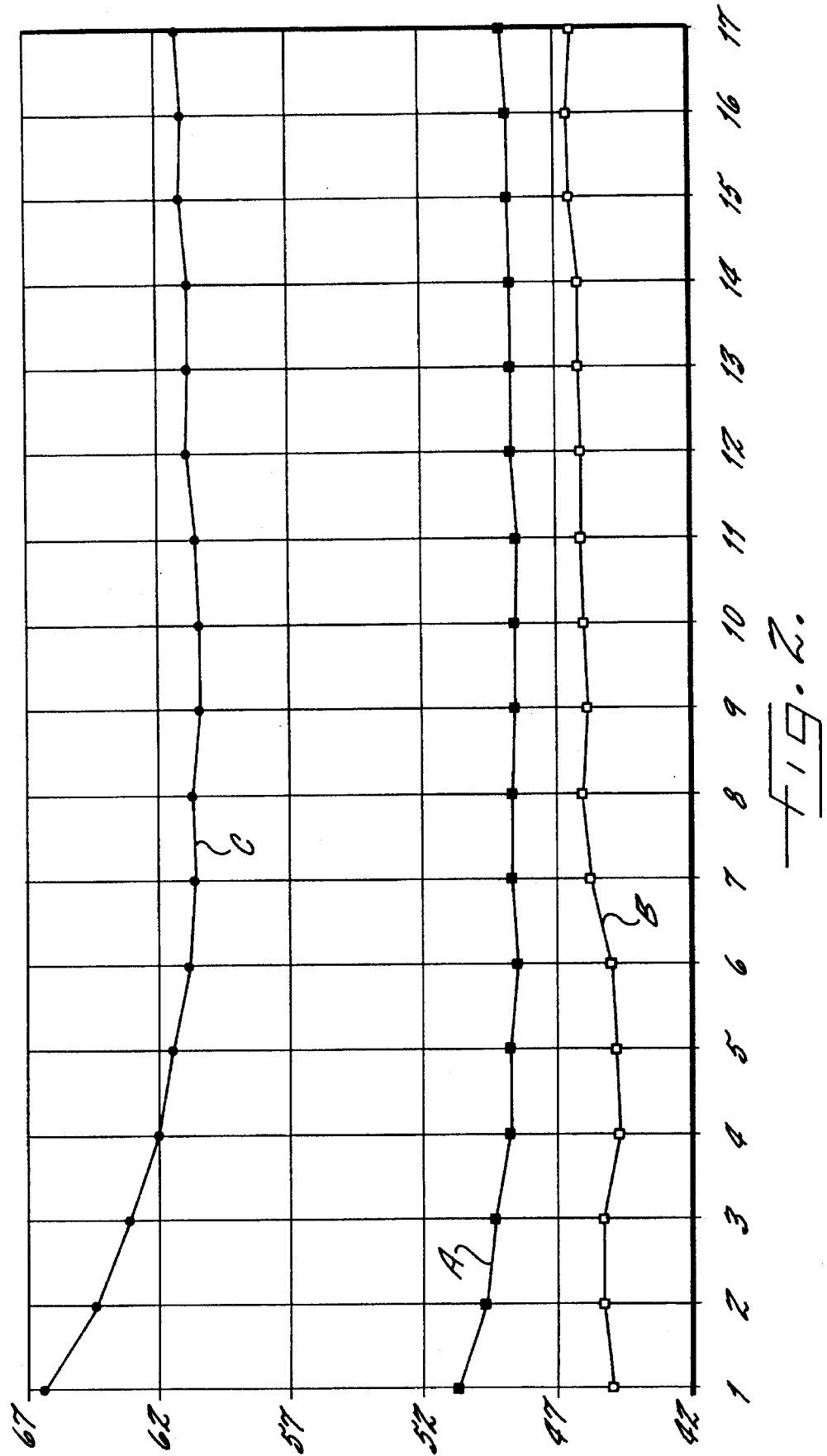
FIG. 2 illustrates the results of a test on the effect on leaving air temperatures of an application of the composition of the present invention to a cooling coil.
Figure 3:
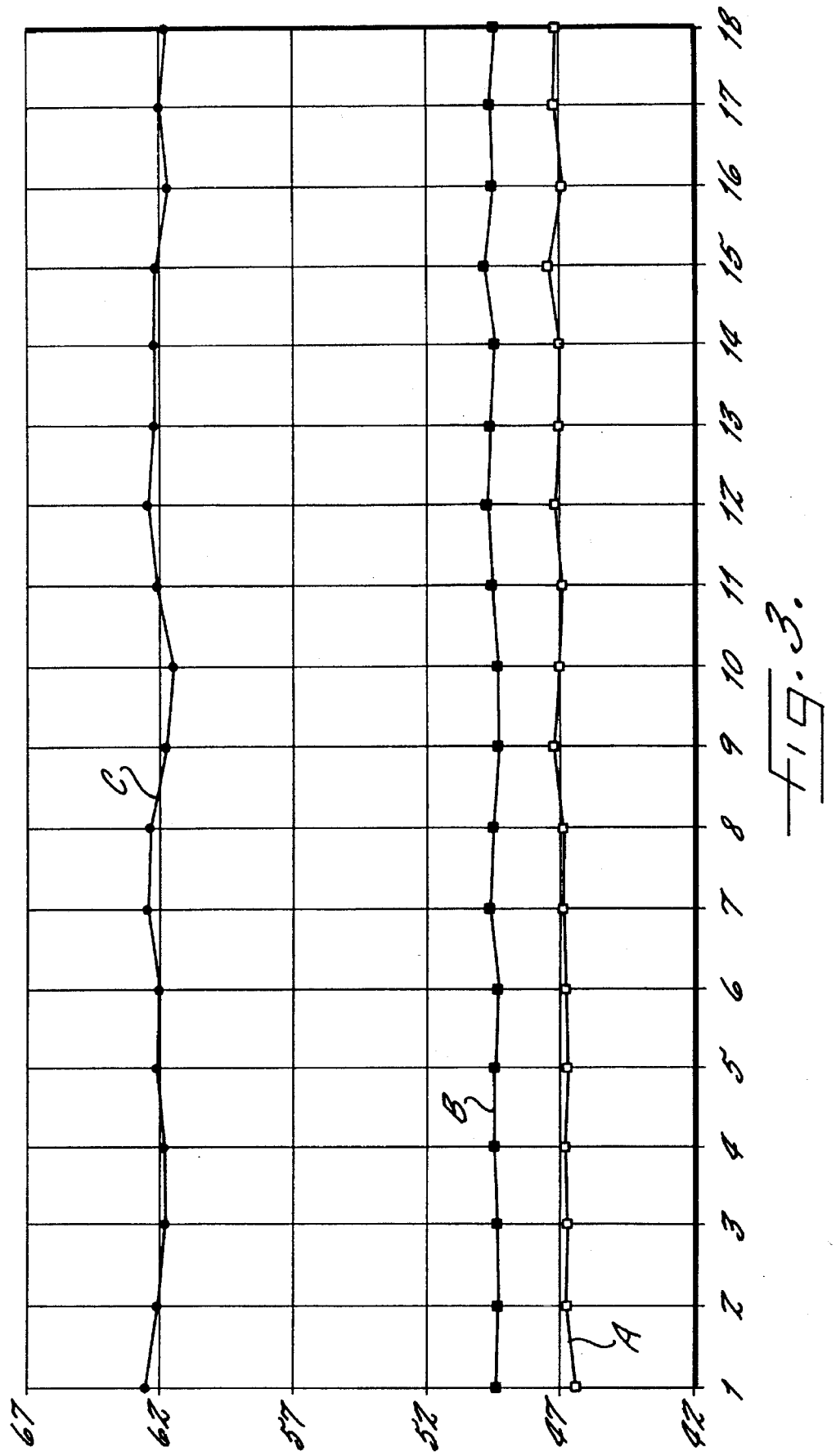
FIG. 3 shows the results of a test as in FIG. 1, the composition having been applied to a cooling coil and a rear coil.

The preferred embodiment of the present invention will now be described with reference to FIGS. 1–5.

COMPOSITION OF THE PREFERRED EMBODIMENT

The composition of an antimicrobial coating for heat exchangers comprises a base that adheres to heat exchanger surfaces, the viscous base comprising a high-solids oil-in-water emulsion based upon an amino functional polysiloxane. In the preferred embodiment, the base comprises T-Guard 104HS (Taylor Chemical Co., Inc., Lawrenceville, Ga.), which imparts a high-gloss silicone film with good adhesion to metallic substrates and further has water-beading, detergent, and weather-resistant properties.

The preferred embodiment for the coating composition further comprises an antimicrobial agent having two active ingredients. The first is a broad-spectrum antimicrobial effective against bacteria, yeasts, and fungi, specifically a 1,2-dibromo-2,4-dicyanobutane product, Tektamer 38 (Calgon Corp., Pittsburgh, Pa.). The second is a fungicide that controls mildew, 2-(4-thiazolyl)benzimidazole, Metasol TK-100 Calgon Corp., Pittsburgh, Pa.). An antifoaming agent may also be added to assist in the mixing process, such as Tego Foamex 800 (Goldschmidt Chemical Corp., Hopewell, Va.).

The preferred embodiment of the formula for the composition of the present invention, which is formed by mixing well for 15 min. under good agitation, has the proportions shown in the following table:

| Product | lbs./100 gal. |
| --- | --- |
| T-Guard 104HS | 100.00–300.00 |
| Water | 500.00–600.00 |
| Tektamer 38 | 0.25 |
| Metasol TK-100 | 2.80 |
| Tego Foamex 800 | 0.00–0.50 |

These values were arrived at after a great deal of experimentation to optimize coverage and applicability. For example, a composition having a range of T-Guard below that shown provides inadequate silicone coverage of the surfaces to be treated; a composition having a range of T-Guard above that shown is too viscous and is difficult to apply.

The concentrations of Tektamer and Metasol were chosen to comply with the manufacturer's recommendations. Too little of either product will reduce the efficacy of the composition's biocidal properties; too much could exceed Environmental Protection Agency limits, although OSHA has not established an upper limit on the active ingredients in these products.

The method of application of the above-described composition solves several of the problems encountered in prior systems. As mentioned, the forming of a film on cooling coils reduces the heat transfer characteristics of an HVAC system and can lead to reduced efficiency and, ultimately, compressor burnout.

Prior to the application of the composition of the present invention, the surface is thoroughly cleaned with a highly alkaline cleaner, triple rinsed, and dried completely. A neutralizing agent may be used if litmus paper indicates pH values greater than 8.0. After rinsing well to ensure surface pH values less than 8.0, the coil is allowed to dry completely. No oils or dirt may remain on the heat exchange surfaces to be treated, nor soap, acid, or caustic residues. The cleaning and rinsing should be conducted at ambient temperature or above so that no further condensation will occur.

Figure 4:
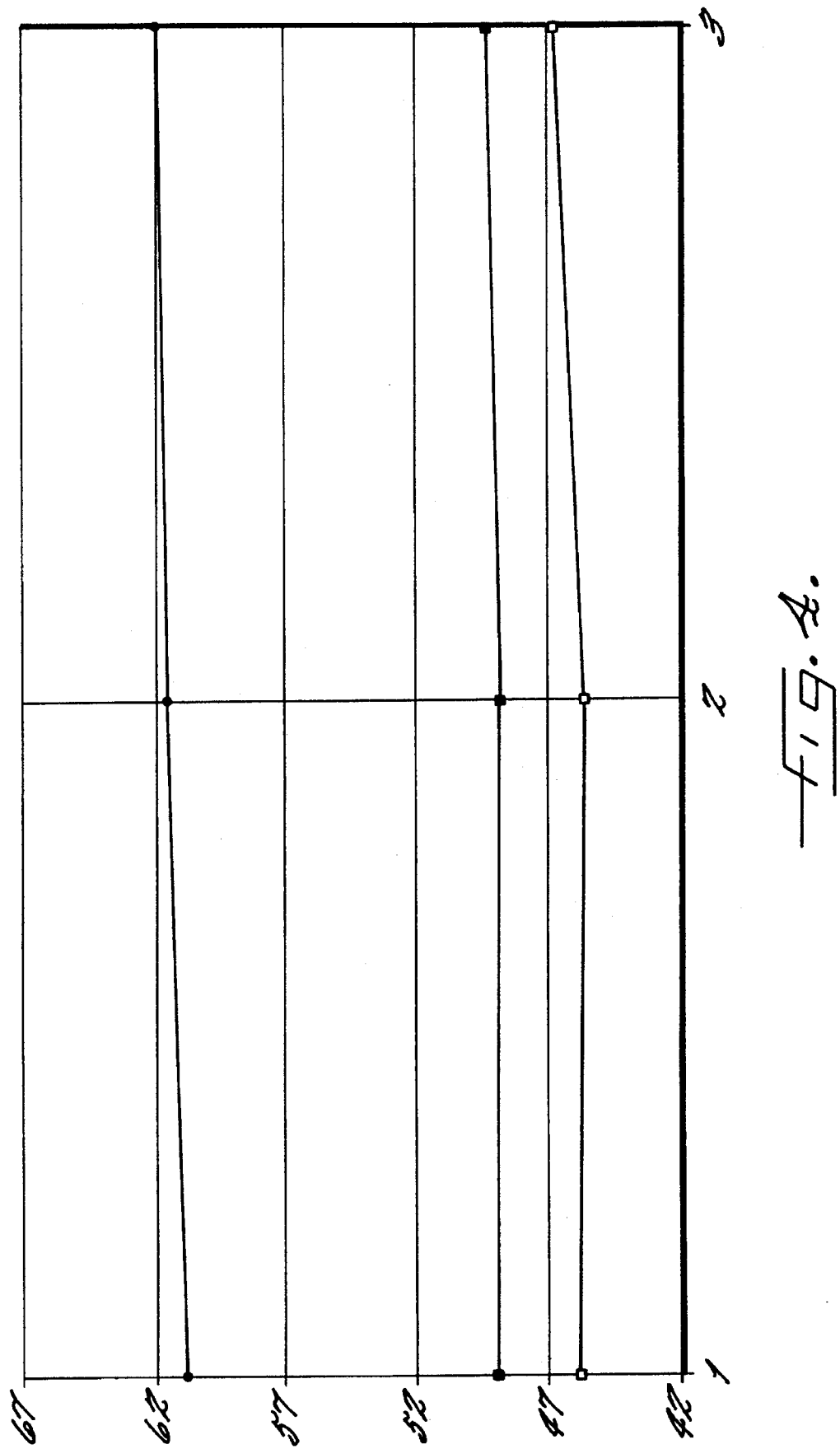
FIG. 4 is a composite of FIGS. 1–3, indicating the effects on the heat transfer characteristics of one and two applications of the composition of the present invention.
Figure 5:
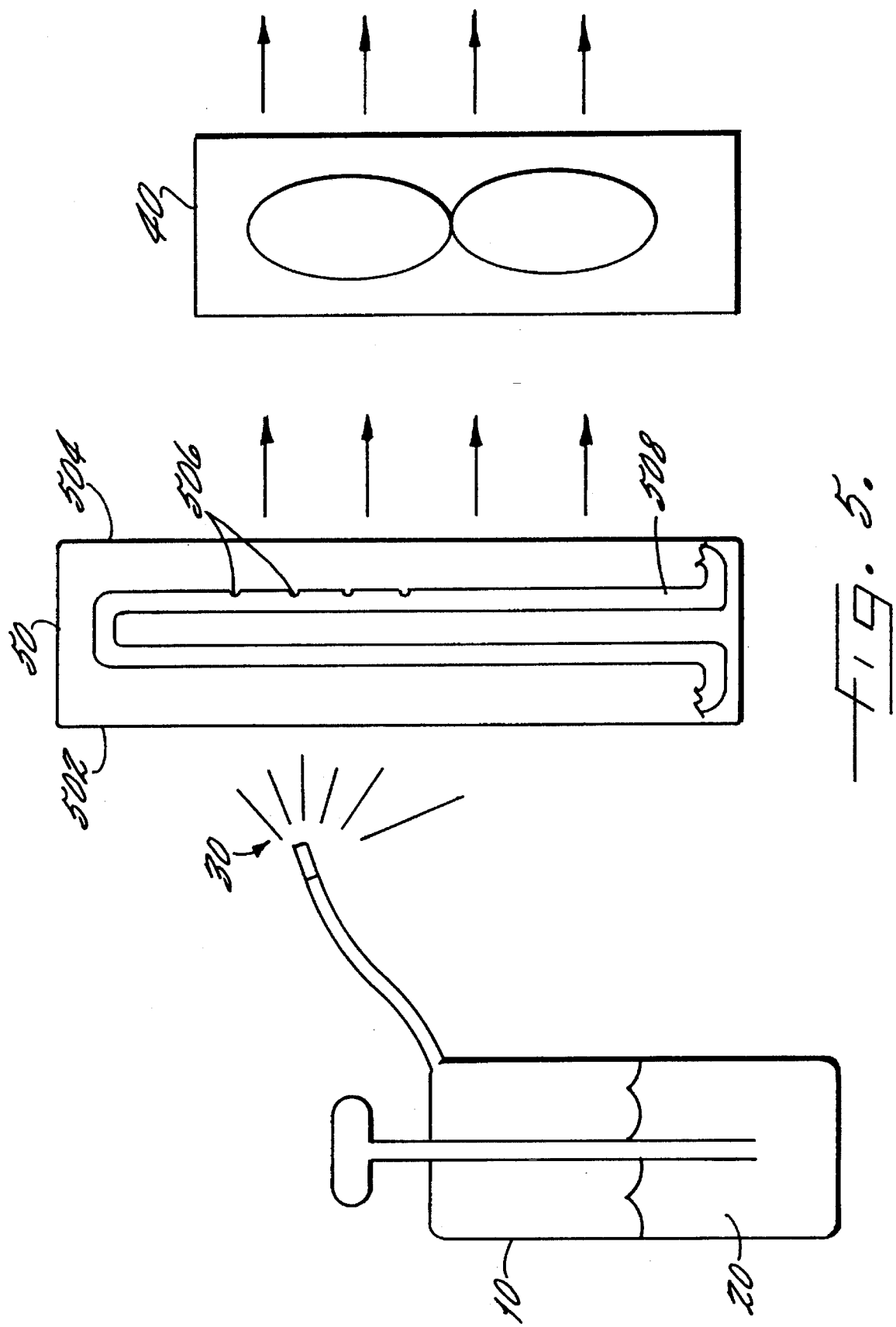
FIG. 5 is a schematic diagram of the application method of the present invention.

The preferred embodiment of the application method, illustrated schematically in FIG. 5, comprises applying the composition 20 to the inlet side 502 of the cooling coil 50 of an HVAC system with a pump-up sprayer 10, which turns the liquid of the composition into a mist 30. A fan 40 is placed on the outlet side 504 of the coil 50 to pull the mist 30 through the coil 50, thus ensuring that the composition 20 is drawn across the heat exchange surface in an air stream. The composition is then dried on the surface, on which it forms a low-friction, antimicrobial barrier, filling the microscopic pittings 506 and adhering to the coil surfaces 508 without completely covering the surface.

The procedure outlined above is then repeated on each coil desired to be treated.

The composition has been designed to cover the microscopic pitting found on coil surfaces and surfaces themselves while not interfering with heat transfer characteristics. Tests have been conducted to ascertain that this was indeed the case, and the results are shown in FIGS. 1–4.

FIG. 1 is the control graph, illustrating the temperature entering the coil, that leaving the coil, and the leaving air temperature. The temperature values, listed on the ordinate, are in deg F. The abscissa represents time, with each reading being taken at approximately 4-minute intervals.

FIGS. 2 and 3 are graphs as for FIG. 1, but for systems having had one coat of the composition applied to the cooling coil (FIG. 2) and having had one coat of the composition applied to the cooling coil and the rear coil (FIG. 3).

A composite graph is shown in FIG. 4, illustrating the effects of applications as for FIGS. 2 and 3 on the average temperatures entering the coil (open squares), leaving the system (solid squares), and leaving the coil (solid circles) for no application, an application to the cooling coil, and an application to the cooling coil and the rear coil. In summary, it can be seen that an application to the cooling coil has no material effect on leaving air temperatures. Specifically, the change in temperatures between the air entering the coil and that leaving the coil varied by less than 1 deg F. in all three tests.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. An antimicrobial coating composition for heat exchangers, comprising:

a base comprising a high-solids oil-in-water emulsion based upon an amino functional polysiloxane having properties for adhering to all surfaces of a heat exchanger without substantially altering the heat exchange properties thereof, the base present in a general range of 100–300 pounds per 100 gallons;

a bacteriostatic and fungistatic agent containing 1,2-dibromo- 2,4-dicyanobutane present in sufficient concentration to prevent growth of bacteria and fungi on the heat exchanger surfaces, the concentration approximately 0.25 pounds per 100 gallons;

a fungicide containing 2-(4-thiazolyl)benzimidazole present in sufficient concentration to prevent growth of fungi on the heat exchanger surfaces in cooperation with the bacteriostatic and fungistatic agent, the concentration approximately 2.8 pounds per 100 gallons; and an antifoaming agent for aiding in mixing the composition ingredients, the antifoaming agent present generally in the range of 0.01–0.5 pounds per 100 gallons.

2. A method for treating a heat exchange surface in air conditioning equipment to reduce the collection of debris and the growth of microbes on the heat exchange surface, the method comprising the,steps of:

providing a composition comprising:

a base comprising a high-solids oil-in-water emulsion based upon an amino functional polysiloxane having properties for adhering to all surfaces of a heat exchanger without substantially altering the heat exchange properties thereof, the base present in a general range of 100–300 pounds per 100 gallons;

a bacteriostatic and fungistatic agent containing 1,2-dibromo-2,4-dicyanobutane present in sufficient concentration to prevent growth of bacteria and fungi on the heat exchanger surfaces, the concentration approximately 0.25 pounds per 100 gallons; and a fungicide containing 2-(4-thiazolyl)benzimidazole present in sufficient concentration to prevent growth of fungi on the heat exchanger surfaces in cooperation with the bacteriostatic and fungistatic agent, the concentration approximately 2.8 pounds per 100 gallons; and applying the composition onto the heat exchange surface to form a low-friction, antimicrobial partial film thereon.

3. The method recited in claim 2, wherein the applying step comprises drawing the composition across the heat exchange surface in an air stream.

4. The method recited in claim 2, wherein the composition comprises a liquid, and wherein the applying step further comprises the step of drying the liquid composition onto the heat exchange surface.

5. The method recited in claim 4, wherein the drawing the composition across the heat exchange surface in an air stream comprises forming a mist of the composition, introducing the mist across an inlet side of the heat exchange surface, and providing a fan at an outlet side of the heat exchange surface directed to draw the mist therethrough.

6. The method recited in claim 2, further comprising a step prior to the applying step comprising thoroughly cleaning the heat exchange surface with an alkaline cleaner, rinsing, and drying the heat exchange surface thereafter.

7. An antimicrobial coating composition for heat exchangers comprising:

a base comprising a high-solids oil-in-water emulsion based upon an amino functional polysiloxane having properties for adhering to all surfaces of a heat exchanger without substantially altering the heat exchange properties thereof, the base present in a general range of 100–300 pounds per 100 gallons;

a bacteriostatic and fungistatic agent containing 1,2-dibromo- 2,4-dicyanobutane present in sufficient concentration to prevent growth of bacteria and fungi on the heat exchanger surfaces, the concentration approximately 0.25 pounds per 100 gallons; and a fungicide containing 2-(4-thiazolyl)benzimidazole present in sufficient concentration to prevent growth of fungi on the heat exchanger surfaces in cooperation with the bacteriostatic and fungistatic agent, the concentration approximately 2.8 pounds per 100 gallons.

* * * * *